(12) United States Patent
Robin et al.

(10) Patent No.: US 6,987,103 B2
(45) Date of Patent: Jan. 17, 2006

(54) TREATMENT OF CHRONIC MYELOGENOUS LEUKMIA, RESISTANT OR INTOLERANT TO ST1571, INVOLVING HOMOHARRINGTONINE ALONE OR COMBINED WITH OTHER AGENTS

(75) Inventors: Jean-Pierre Robin, Charlottesville, VA (US); François-Xavier Mahon, Bordeaux (FR); Hervé Maisonneuve, La Roche sur Yon (FR); Frederick Maloisel, Illkirch Graffenstaden (FR); Julie Blanchard, Rouillon (FR)

(73) Assignee: Stragen Pharma S.A., Geneva (CH)

( * ) Notice: Subject to any disclaimer, the term of this patent is extended or adjusted under 35 U.S.C. 154(b) by 296 days.

(21) Appl. No.: 10/397,267

(22) Filed: Mar. 27, 2003

(65) Prior Publication Data

US 2004/0019036 A1    Jan. 29, 2004

Related U.S. Application Data

(63) Continuation-in-part of application No. PCT/IB02/03992, filed on Sep. 5, 2002.

(60) Provisional application No. 60/316,967, filed on Sep. 5, 2001.

(51) Int. Cl.
A61K 31/55    (2006.01)
A61K 31/505   (2006.01)
A61K 31/70    (2006.01)
A61K 38/21    (2006.01)

(52) U.S. Cl. ................... 514/214.01; 514/49; 514/275; 424/85.7

(58) Field of Classification Search ........... 514/214.01, 514/275, 49; 424/85.7
See application file for complete search history.

(56) References Cited

U.S. PATENT DOCUMENTS

2003/0148955 A1 * 8/2003 Pluenneke ................... 514/12

OTHER PUBLICATIONS

Cancer Principles & Practice of Oncology, 5th Edition, published 1997 by Lippincott-Raven, pp 498-509.*
Cancer Principles & Practice of Oncology, 6th Edition, published 2001 by Lippincott-Raven, pp 2433-2445.*
Tipping et al. Blood, (Nov. 16, 2000), vol. 96, No. 11, Part 1, pp 98a. print. Meeting Info.: 42 Annual Meeting of the American Society of Hematology, San Francisco, California, USA Dec. 1-5, 2000. American Society of Hematology (Abstract Only).*
Hagop M. Kantarjian, et al, "Chronic Myeiogenous Leukemia-Progress at the M.D. Anderson Cancer Center over the Past Two Decades and Future Directions: First Emil J. Freireich Award Lecture," Clinical Cancer Research, vol. 3, Dec. 1997, pp. 2723-2733.
Hagop M. Kantarjian, MD, et al, "Clinical Course and Therapy of Chronic Myelogenous Leukemia with Interferon-Alpha and Chemotherapy," Biology and Therapy of Chronic Myelogenous Leukemia, vol. 12, No. 1, Feb. 1998, pp. 31-80.
Jorge E. Cortes, MD, et al, "Chronic Myelogenous Leukemia: A Review," The American Journal of Medicine, vol. 100, May 1996, pp. 555-570.
Stefan Faderl, MD, et al, "Chronic Myelogenous Leukemia: Update on Biology and Treatment," Oncology, vol. 13, No. 2, Feb. 1999, pp. 169-180.
James N. George, et al, "The Evidence-Based Analysis of Treatment for Chronic Myeloid Leukemia: An Introduction to Its Methods and Clinical Implications," Blood, vol. 94, No. 5, Sep. 1, 1999, pp. 1515-1517.
Richard T. Silver, et al, "An Evidence-Based Analysis of the Effect of Busulfan, Hydroxyurea, Interferon, and Allogeneic Bone Marrow Transplatation in Treating the Chronic Phase of Chronic Myleoid Leukemia: Developed for the American Society of Hematology," Blood, vol. 94, No. 5, Sep. 1, 1999, pp. 1517-1536.
Jean L. Grem, et al, "Cephalotaxine Esters: Antileukemic Advance or Therapeutic Failure," Journal of the National Cancer Institute, vol. 80, No. 14, Sep. 21, 1988, pp. 1095-1103.
William J. Slichenmyer, MD, et al, "New Natural Products in Cancer Chemotherapy," J. Clin. Pharmacol., vol. 30, 1990, pp. 770-788.
Alex J. Tipping, et al. Abstract #420, "Response of STI571-Resistant Cells to other Chemotherapeutic Drugs and Signal Transduction Inhibitors," Molecular Pharmacology & Drug Resistance, p. 98a. (2003).
Barbara Scappini, et al. Abstract #425, "In Vitro Effects of STI571-Containing Drug Combinations on Growth of Ph-Positive Myelogenous Leukemia-Derived Cells," Molecular Pharmacology & Drug Resistance, p. 99a. (2003).

(Continued)

Primary Examiner—Raymond J. Henley, III
(74) Attorney, Agent, or Firm—Buchanan Ingersoll PC

(57) ABSTRACT

The present invention concerns a method of treating chronic myelogenous leukemia, a related myeloproliferative disorder or a Ph-positive acute lymphocytic leukemia in a subject animal, comprising:
(a) selecting or identifying an animal suffering from chronic myelogenous leukemia or a related myeloproliferative disorder and showing resistance or intolerance to treatment with STI571; and
(b) administering to the animal homoharringtonine.

In a preferred embodiment, the animal is a human being.

25 Claims, 5 Drawing Sheets

OTHER PUBLICATIONS

Yasuhiko Kano, et al, "In vitro cytotoxic effects of a tyrosine kinase inhibitor STI571 in combination with commonly used antileukemic agents," Blood, vol. 97, No. 7, Apr. 1, 2001, pp. 1999-2007.

Barbara Scappini, MD, et al, "In Vitro Effects of STI 571-Containing Drug Combinations on the growth of Philadelphia-Positive Chronic Myelogenous Leukemia Cells," Cancer, vol. 94, No. 10, May 15, 2002, pp. 2653-2662.

AJ Tipping, et al, "Drug responses of imatinib mesylate-resistant cells: synergism of imatinib with other chemotherapeutic drugs," Leukemia, vol. 16, 2002, pp. 2349-2357.

Z. Cai, et al, "Apoptotic response to homoharringtonine in human wt p53 leukemic cells is independent of reactive oxygen species generation and implicates Bax translocation, mitochondrial cytochrome c release and caspase activation," Leukemia, vol. 15, 2001, pp. 567-574.

Martin Sattler, et al, "The BCR/ABL Tyrosine Kinase Induces Production of Reactive Oxygen Species in Histamine Cells," The Journal of Biological Chemistry, vol. 275, No. 32, Aug. 11, 2000, pp. 24273-24278.

Metello Iacobini, et al, "Involvement of oxygen radicals in cytarabine-induced apoptosis in human polymorphonuclear cells," Biochemical Pharmacology, vol. 61, 2001, pp. 1033-1040.

Kristoffer Hellstrand, et al, "Histamin and Cytokine Therapy," Acta Oncologica, vol. 37, No. 4, 1998, pp. 347-353.

Ting-Chao Chou, et al, "Quantitative Analysis of Dose-Effect Relationships: The Combined Effects of Multiple Drugs or Enzyme Inhibitors," Adv. Enzyme Regul, vol. 22, 1984, pp. 27-55.

*Gleevec*™ (imatinib mesylate), Prescribing Information: Sponsor's Brochure T2002-97, 89012404, Dec. 2002, pp. 1-21, Novartis Pharma AG, Basle, Switzerland.

* cited by examiner

Study HS2b: A multicenter phase II single-arm study [1] of Sequential Addition of HHT, In Patients with an ongoing treatment by STI571, for AP of CML, who lost or failed to have a major hematologic response [2]

Inclusion Criteria
Patients with an ongoing STI571 therapy for AP CML for 2 months or more, who lost or failed to have MHR (i.e. CHR/NEL) [2]. Pts refractory to STI571 (i.e. No PBR)[3] are not eligible. No extramedullar disease. No prior HHT or Intensive Chemotherapy for CML.

Stratification
1. *Age:* cutoff 60
2: *Existing partial responses*
   - RCP: 5-15%BM and PB blasts
   - PBR: <5% PB blasts [3]

Treatment: Add HHT to STI571[4]

Half-dose HHT: 2.5 mg/m$^2$/day, D1-D7/ 28 days
Half-dose STI 400 mg daily$^2$, then adjust [5] both agents on myelosuppression: 1-day step per cycle for HHT *and* 100 mg daily step for STI [6]

MHR at 4 months [7]
(Expected: >40%)

Assessment
MHR rate after HHT addition as primary end point for accelerated approval request.

FIG. 5

TREATMENT OF CHRONIC MYELOGENOUS LEUKMIA, RESISTANT OR INTOLERANT TO ST1571, INVOLVING HOMOHARRINGTONINE ALONE OR COMBINED WITH OTHER AGENTS

This application is a continuation-in-part of International Application No. PCT/IB02/03992, filed on Sep. 5, 2002, which application claims priority to U.S. Provisional Application No. 60/316,967, filed on Sep. 5, 2001, the entire contents of which are hereby incorporated by reference.

The invention relates to methods for treating subjects suffering from chronic myelogenous leukemia which is resistant or intolerant to treatment with STI571, involving treating the subjects with homoharringtonine alone or combined with STI571 and/or other antileukemic agents.

Chronic myelogenous leukemia (CML) is a mycloproliferative disease which strikes about 4,500 new cases per year in the U.S. or in Europe. The median survival of this disease is around 3 years without treatment. Since the introduction of standard therapy by interferon alpha (INF) the median survival of this leukemia reaches about 7 years. However when patients become resistant to interferon, progression to acute phases occurs. Until these recent years there were only a few drugs able to induce a new remission. [Ref 1–5] Homoharringtonine, an alkaloid isolated from the genus *Cephalotaxus* [Ref 1, 2, 6, 7] and more recently STI571, a synthetic product, are recent drugs able to give a new remission to patients resistant to INF. Moreover STI571 was recently approved in the U.S. as major therapy of CML.

STI571 is becoming the standard of therapy for CML; recent clinical studies indicate that good results are obtained in patients with chronic phase CML: >90% of complete hematologic response, including 50% of cytogenetic response. However, limited result are seen in accelerated phase (<40%), and poor efficacy is obtained in blastic phase (<10% of complete bematologic response) including very transient remission. [Ref 8] In addition, after 15 months on STI571, we recently found that actuarial risk of progression to accelerated phase or blastic phase was higher than 30% [Ref 9] (unpublished results). To overcome these therapeutic limitations, combinations of STI571 with existing standard therapy based on INFs (including new form of TNF such as PEG INF) were recently tried. Preliminary analysis of these combinations indicates that addition of TNF or PEG INF does not change really the efficacy of each drug given alone. [Ref 9] (unpublished results)

There is therefore a need for improved methods of treating CML which provide longer term remission. In view of the limitations of STI571, there is a need for therapies providing improved results in the treatment of accelerated phase CML and blastic phase.

It was recently published that STI571 and homoharringtonine combination exhibit additive or synergistic cytotoxic effect in vitro, [Ref 10–13] which allows their clinical use as combination. In another preliminary study, it was indicated that homoharringtonine exhibits activity in a standard myeloid cell line made resistant in vitro to STI571.

We discovered recently that cells coming from patients with chronic myelogenous leukemia resistant to STI571, exhibited a good sensibility to homoharringtonine. [14] (unpublished results). We also found that patients resistant or intolerant to STI571 exhibit hematologic response to homoharringtonine, and furthermore that this response is sometimes transient (Robin J P et al., unpublished results). This finding could be explained by the rapid appearance of new malignant clones in which an alternate mechanism of apoptosis inhibition was "found" by a mutation-selection process of leukemic cells.

Further support for such a mechanism can be found in recent articles which indicate that the two drugs induce a release of the inhibition of caspase (a key molecular signal in the triggering of apoptosis) according two different alternative pathways:

First, for homoharringtonine, independent of reactive oxygen species (ROS) generation; [Ref 15]

Second, for STI, ROS dependent; [Ref 16]

In addition, Ara-C, a fourth agent currently combined with both INF, homoharringtonine and more recently STI571, induce apoptosis according to a ROS dependent mechanism [Ref 17]. (Some findings indicate that interferon alpha cytotoxicity would act according to a ROS dependent mechanism [Ref 18]).

This indicates that homoharringtonine may be use as new treatment of patients resistant to CML but also that standard methods of treatment which includes removing the existing resistant therapy and replace it by the new putatively active one should by improved.

The present invention is based on the discovery that the treatment of CML using the combination of STI571 and homoharringtonine resulted in improved treatment outcomes, and that treatment with homoharringtonine results in effective treatment of CML which is resistant or intolerant to STI571. The invention is also based on the discovery that treatment of CML using first STI571 and then homoharringtonine in the absence of STI571 may lead to a transient response.

The invention provides a novel method of treatment of patients with chronic myelogenous leukemia, other related myeloproliferative diseases and Ph-positive acute lymphocytic leukemia involving homoharringtonine based therapy in order to overcome primary or secondary resistance and/or intolerance to STI571, and able to induce or to improve hematologic response and/or cytogenetic response and, eventually, survival, with a mild non hematologic toxicity. Homoharringtonine is preferably combined with one or more other antileukemic agents including STI571 itself. In other embodiments, homoharringtonine is combined simultaneously with one or more other antileukemic agents including STI571 itself which is continued. In other aspects, homoharringtonine can be combined sequentially with one or more other antileukemic agents, optionally including STI571 itself which is continued. In other aspects of these methods, homoharringtonine can be combined sequentially by addition to existing STI571 therapy including in patients who lost their response to or who failed to respond to this agent in using the following steps (a) to (d), optionally (e): (a) patients with chronic myelogenous leukemia, eventually resistant to standard interferon alpha therapy, are treated by STI571 (400 to 800 mg daily, permanently) until a complete cytogenetic response (for de novo patients) or at least a complete hematologic response (for all other more advanced phases) are obtained, (b) in these partially STI571-resistant patients, STI571 is not removed but only reduced to 300 to 400 mg daily, in those of patients who failed to have or lost their complete cytogenetic or hematologic response, (c) homoharringtonine is administered subcutaneously and/or intravenously or/and orally, at dose 0.25 to 5 mg/m$^2$ preferably at dose 2.5 mg/m$^2$, preferably for 2 to 14 days per 28-day cycle, (d) finally homoharringtonine dose and/or STI571 are adjusted according to cytopenia and/or side effects; and (e) optionally, subcutaneous or intravenous or oral nucleoside synergistic with homoharringtonine, preferably cytarabine may be simultaneously or sequentially added to homoharringtonine.

The present invention concerns a method of treating chronic myelogenous leukemia, a related myeloproliferative disorder or a Ph-positive acute lymphocytic leukemia in a subject animal, comprising:
(a) selecting or identifying an animal suffering from chronic myelogenous leukemia or a related myeloproliferative disorder and showing resistance or intolerance to treatment with STI571; and
(b) administering to the animal homoharringtonine.

The present invention further relates to a method of treating chronic myelogenous leukemia or a related myeloproliferative disorder in a subject animal, comprising (a) selecting or identifying an animal suffering from chronic myelogenous leukemia or a related myeloproliferative disorder or Ph-positive acute lymphocytic leukemia and showing resistance or intolerance to treatment with STI571; and (b) administering to the animal homoharringtonine in an amount effective to inhibit proliferation of myeloid cells. In certain embodiments, homoharringtonine and STI571 and/or other antileukemic agents are administered in combinations more preferably homoharringtonine is added to a therapeutic regimen comprising STI571 without discontinuing the STI571 treatment. In other embodiments homoharringtonine and STI571 and/or other antileukemic agents are administered in a sequential treatment.

In a preferred embodiment, the homoharringtonine is combined with one or more other antileukemic agents including STI571. Preferably, homoharringtonine is combined simultaneously with one or more other antileukemic agents including STI571. More preferably, homoharringtonine is combined simultaneously with one or more other antileukemic agents including STI571, wherein STI571 is continued from previous treatment.

In another preferred embodiment, homoharringtonine is combined sequentially with one or more other antileukemic agents. Preferably, homoharringtonine is combined sequentially with one or more other antileukemic agents including STI571 itself which is continued.

The present invention also embodies a method for inhibiting proliferation of a hyperproliferative myeloid cell, as well as to a method of treating CML or a related myeloproliferative disorder in a subject animal, comprising: a) contacting said cell with or administering to said animal STI571; and b) contacting said cell with, or administering to said animal, homoharringtonine. Accordingly, the invention also relates to a method of preventing resistance to STI571, in a subject animal suffering from CML or a related myeloproliferative disorder. In further preferred embodiments, the methods of the invention further comprise treating said hyperproliferative myeloid cell or animal with one or more other therapeutic antileukemic compounds, preferably in sequential treatment. Several examples of suitable compounds are further mentioned herein. The STI571 and homoharringtonine will preferably be administered in an amount effective to inhibit proliferation of myeloid cells.

Therefore, the present invention concerns also a method of treatment, wherein homoharringtonine is combined sequentially by addition to existing STI571 therapy, including in patients who lost their response to or who failed to respond to STI571, comprising the following steps (a) to (d), and optionally (e):
(a) administering to patients with chronic myelogenous leukemia, optionally resistant to standard interferon alpha therapy, STI571 (preferably at 400 to 800 mg daily, permanently) until a complete cytogenetic response (preferably for de novo patients) or at least a complete hematologic response (preferably for all other more advanced phases) is obtained,
(b) in these partially STI571-resistant patients, reducing to 300 to 400 mg daily but not removing STI571 treatment, in those patients who failed to have or lost their complete cytogenetic or hematologic response,
(c) administering homoharringtonine subcutaneously and/or intravenously or/and orally, at dose 0.25 to 5 mg/m$^2$, preferably at dose 2.5 mg/m$^2$, preferably for 2 to 14 days per 28-day cycle;
(d) adjusting the homoharringtonine dose and/or STI571 dose according to cytopenia and/or side effects;
(e) optionally, subcutaneously or intravenously administering an oral nucleoside synergistic with homoharringtonine, wherein said oral nucleoside may be added simultaneously or sequentially to homoharringtonine.

In a preferred embodiment, said oral nucleoside in step (c) is cytarabine, wherein cytarabine may be added simultaneously or sequentially to homoharringtonine.

In another embodiment, the present invention concerns a method for inhibiting proliferation of a hyperproliferative myeloid cell resistant to STI571, comprising:
a) contacting the cell with STI571; and
b) contacting the cell with homoharringtonine,
wherein STI571 and homoharringtonine are provided in an amount effective to inhibit proliferation of said myeloid cell.

In a further embodiment, the present invention concerns a method of treating chronic myelogenous leukemia, a related myeloproliferative disorder or a Ph-positive acute lymphocytic leukemia in a subject animal:
a) administering to the animal in a first course of treatment STI571, wherein said CML or disorder displays resistance and/or intolerance to STI571;
b) administering to the animal in a second course of treatment a combination of homoharringtonine and STI571 in an amount effective to inhibit proliferation of myeloid cells.

The (hyperproliferative) myeloid cell or myeloproliferative disorder will preferably be characterized as being resistant and/or intolerance to STI571, that is, STI571 when not combined with homoharringtonine. Preferably the efficacy of the therapy is enhanced through synergistic effects of STI571 and homoharringtonine.

Preferably the treatment of the present invention is able to overcome resistance and/or intolerance to STI571.

More preferably said treatment induces a hematologic response, and/or a cytogenetic response and/or survival, with weak non-hematologic toxicity.

In a preferred embodiment the efficacy of the therapy is enhanced through synergistic effects of STI571 and homoharringtonine.

Preferably, the other antileukemic agents are interferon alpha and/or one or more nucleosides and/or a farnesyl transferase inhibitor (FTI).

More preferably, the other antileukemic agent is interferon alpha or PEG-interferon.

More preferably, the other antileukemic agent is a nucleoside. More preferably, the nucleosides are cytarabine (Ara-C) and/or decitabine and/or troxacytabine. More preferably, the nucleoside is cytarabine (Ara-C).

More preferably, the other antileukemic agent is a farnesyl transferase inhibitor (FTI).

More preferably, the other agents are a combination of interferon alpha and cytarabine.

In a preferred embodiment, the animal treated by the treatment of the present invention is a human being.

The present invention also concern the use of Homoharringtonine with other chemotherapeutic agent, in particular STI571, as a combined preparation for simultaneous, separate or sequential use in CML therapy or for treating a related myeloproliferative disorder, advantageously for treating CML or a related myeloproliferative disorder in an animal, advantageously a human being, showing resistance or intolerance to treatment with STI571.

As mentioned, STI571 and homoharringtonine can be administered during the same course or cycle of treatment. In one embodiment they can be coadministered, optionally substantially simultaneously, optionally as a single pharmaceutical composition. The methods of the invention may also involve the administration of STI571 and homoharringtonine to an animal such as a human patient who has not been previously treated with STI571. Preferably, however, the STI571 and homoharringtonine are administered to an animal which has undergone a first course or cycle of therapy for the treatment of the myeloproliferative disorder. In related aspects, the inventions also comprise methods of treatments where more than one course of therapy is carried out. Included is a method of treating CML or a related myeloproliferative disorder or Ph-positive acute lymphocytic leukemia in a subject animal comprising: a) administering to the animal in a first course or cycle of treatment STI571; and b) administering to the animal in a second course or cycle of treatment a combination of homoharringtonine STI571 in an amount effective to inhibit proliferation of the cell. Generally this method will be used when said subject shows resistance or intolerance to treatment with STI571 in the first course or cycle of treatment.

Said other antileukemic agents that can be used in therapeutic combinations of the invention with homoharringtonine may include interferon alpha (including interferon alpha or PEG-interferon) and/or one or more nucleosides (including cytarabine (Ara-C) and/or decitabine and/or troxacytabine) and/or a farnesyl transferase inhibitor (FTI). In preferred embodiments of the methods of treatment, the other agents are a combination of interferon alpha and cytarabine.

While reference is generally made to STI571 which is currently commercially available as an approved pharmaceutical product, and for which particularly surprising results were obtained using the methods of the invention, it will be appreciated that the invention also applies to other related agents, including other protein kinase inhibitors, more preferably protein tyrosine kinase inhibitors such as Bcr-Abl kinase inhibitors, or more preferably other compounds of the 2-phenylaminopyrimidine type.

Advantageously, Homoharringtonine is administrated by subcutaneous administration such as described in the patent application U.S. Ser. No. 09/801,751 which is incorporated by reference. Advantageously, Homoharringtonine is administrated in the form of a salt such as described in the patent application U.S. Ser. No. 09/801,751.

BRIEF DESCRIPTION OF THE DRAWINGS

FIG. 5 is a plan of a multicenter Phase II single arm study of sequential addition of HHT, in patients with an ongoing treatment by STI571 for AP of CML, who lost or failed to have a major hematologic response.

Figure 1:
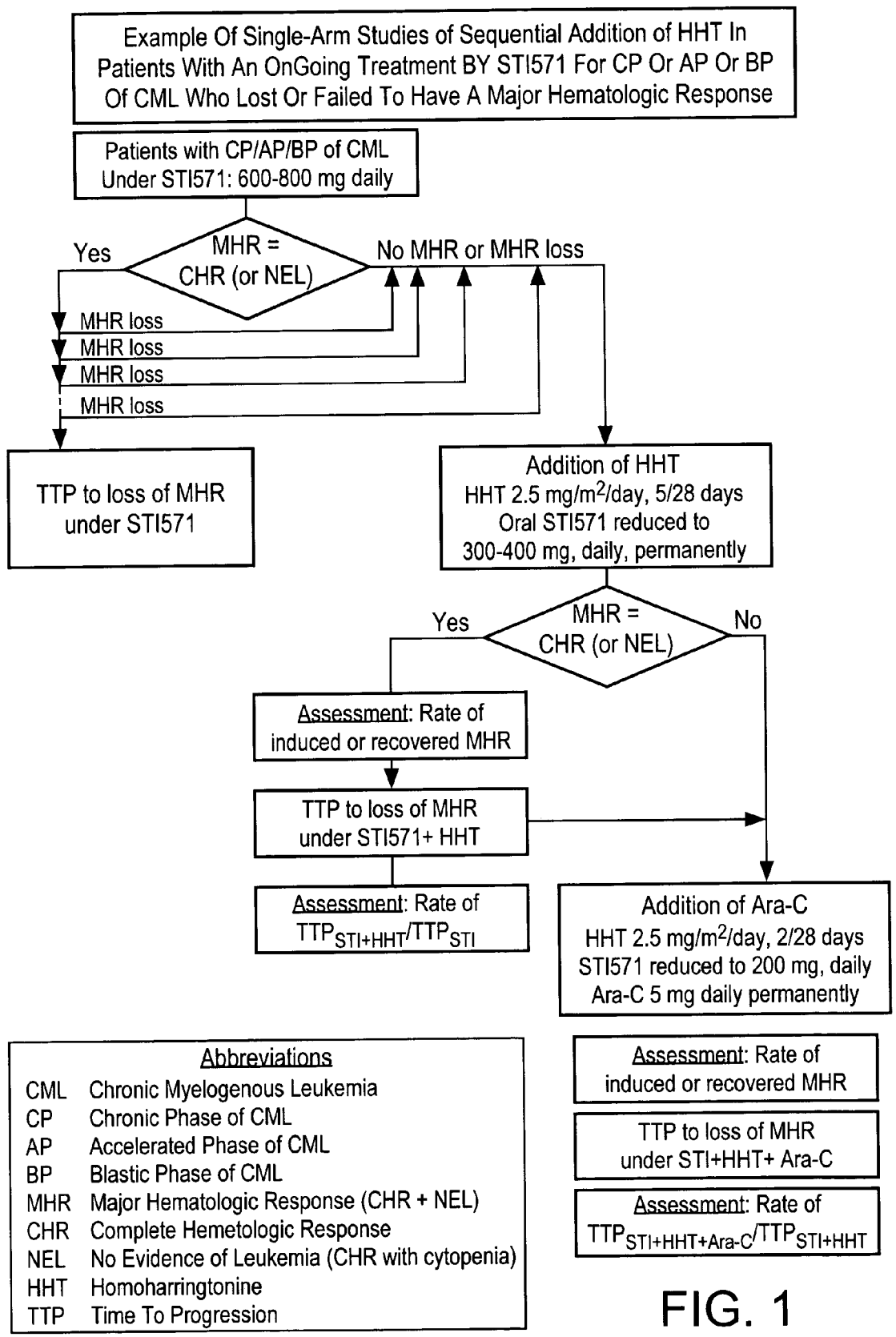
FIG. 1 is a plan of an example of single arm studies of the sequential addition of HHT in patients in an ongoing treatment with STI571 for chronic phase (CP), accelerated phase (AP) or blastic phase (BP) of CML, who lost or failed to have a major hematologic response.

The main aspect of this invention describes a new method of therapy, based on treatment with homoharringtonine and its combination with STI571 plus eventually a third drug such as Ara-C and plus eventually a fourth drug such as interferon alpha, in order to induce a remission or to improve the existing level of hematologic and/or cytogenetic response and, finally, survival in patients (in particular human) with chronic myelogenous leukemia or with other related myeloproliferative disease or with Ph-positive acute lymphocytic leukemia who lost their response with or who failed to respond to or are intolerant to STI571.

Moreover, this invention describes a new regimen of use of homoharringtonine, based on sequential addition of homoharringtonine to existing treatment based STI571 plus eventually another drug such as interferon alpha and/or Ara-C, without stopping existing treatment for which the patient is resistant, able to induce a new remission or to improve the existing level of hematologic and/or cytogenetic response in patients with chronic myelogenous leukemia who failed to have or who lost or decreased their level of hematologic and/or cytogenetic responses to the said existing treatment.

Also, this invention describes a new method of therapy, based on homoharringtonine sequential substitutive combinations of STI571 able to induce a new remission in patients with chronic myelogenous leukemia who failed to have or who lost biological and/or clinical response.

We discovered that leukemic cells of patients with blast crisis of chronic myelogenous leukemia who relapse after treatment by STI571, are sensitive to homoharringtonine: there is no cross resistance between homoharringtonine and STI571.

In addition, we selected two STI571-resistant cell lines in order to analysis the to combination of the two drugs: K562-s and LAMA84-s, two human cell lines exhibiting the feature of chronic myelogenous leukemia. The effect of homoharringtonine was also determined in their STI571-resistant counterparts K-562-r and LAMA84-r, respectively. Homoharringtonine was apparently additive if not mildly antagonistic in K562-s and LAMA84-s, but, surprisingly clearly synergistic in their STI571-resistant counterparts K-562-r and LAMA84-r (see table II of Example 2). In other word, the more a cell line is resistant, the more the addition of homoharringtonine to existing STI571 is synergistic. This observation is unexpected because usually synergistic effect is not related with cross-resistance. The consequence of this observation is one of the key aspects of our invention: homoharringtonine-STI 571 combination is more efficient in patients resistant to STI571 than is patient sensible to this product and this efficacy will be higher if STI571 is maintained during the homoharringtonine administration.

The following method of therapy is used:
patients with chronic myelogenous leukemia resistant or not to standard interferon based therapy are treated by STI571 until complete hematologic response is obtained;
then, those of patients who failed to have or lost their hematologic response are treated by homoharringtonine in using the usual regimen (2.5 mg/m², 5 to 7 days per 28-day cycle) but contrary to the usual practice in chemotherapy, the first drug for which the patient is partially resistant (STI571) is not removed to allow to the synergistic effect to occur;
then those patients who failed to have or lost their hematologic response may be treated by a third agent, preferably cytarabine (Ara-C).

This new sequential additive method of therapy is able to give a large rate of complete hematologic response and the resulting median survival would reach a time never encountered prior to the present invention, hematologic response and the resulting medial survival would reach a time never encountered.

"Cell proliferative disorders" refer to disorders wherein unwanted cell proliferation of one or more subset(s) of cells in a multicellular organism occurs, resulting in harm (e.g., discomfort or decreased life expectancy) to the multicellular organism. Cell proliferative disorders can occur in different types of animals and in humans. Among cell proliferative disorders are myeloproliferative disorders such as CML.

A "therapeutic effect" generally refers to either the inhibition, to some extent, of growth of cells causing or contributing to a cell proliferative disorder. A therapeutic effect relieves to some extent one or more of the symptoms of a cell proliferative disorder. In reference to the treatment of a myeloproliferative disorder, a therapeutic effect can include but is not limited to one or more of the following: 1) reduction in the number of cancer (e.g. leukemia) cells; 2) hematologic response; 3) cytogenetic response; and/or 4) relieving to some extent one or more of the symptoms associated with the disorder.

The compounds of this invention can be administered to a patient alone, or in a pharmaceutical composition comprising the active compound and a carrier or excipient. Formulations, dosages, and methods or administration for the preferred compounds individually will already be available, e.g. the widespread commercial use of STI571and previous studies conducted with homoharringtonine, and methods of administration can be carried out using any suitable manner known in the art, or as described in the examples. Nevertheless, the compounds or pharmaceutical compositions can be administered by different routes, in different formulations or dosages, etc. including but not limited to intravenously, subcutaneously, orally or topically.

Rationale of the Study

As further described below, clinical studies have been designed to examine patients with chronic phase of CML and with an ongoing treatment by STI571 alone, who lost or failed to have a complete hematologic response (CHR) for accelerated and blastic phases) or complete cytogenetic response (CCGR) for chronic phase CML. Patients are randomized for addition of homoharringtonine to STI571 and compared to observation of continuation of ongoing treatment with STI, in control arm. Time to progression to accelerated or blastic phase (after 15 months on STI571, the actuarial risk of progression to AP or BP is >30%) or patient death are used as endpoint for assessment. Optionally the same studies could be performed in using the investigational arm only. Inclusion Criteria are: Philadelphia chromosome positive patients; characteristics of blastic, accelerated or chronic phase; Age >18; no extramedullar disease; No prior homoharringtonine; Patients must have an ongoing treatment for CML for 1 to 4 months or more by STI571 alone therapy at the time of inclusion, and patient must lost or failed to have CCGR or CHR with this ongoing STI571 treatment. Prior INF+/−Ara-C before STI571 is allowed.

Treatment: Patient with an ongoing treatment by STI571 alone for CML are enrolled in the study for randomization between investigational arm for sequential additive homoharringtonine therapy (addition of homoharringtonine to existing STI) or control arm for observation of continuation of STI.

Assessment criteria: Time to progression since the date of addition of homoharringtonine to STI571 alone is compared to continuation of STI571 alone is assessed as primary endpoint to support standard approval. Rate of CHR or CCGR after 2 to 4 months of addition of homoharringtonine to STI571 in investigational arm are compared to continuation of STI571 alone in control arm, as secondary endpoint. In addition, CCGR of each patient of treatment arm is compared to itself before and after addition of homoharringtonine. These two kinds of response comparison of homoharringtonine+STI571 versus STI571 are assessed by interim analyses In the single arm version of such studies, only historical comparison of the rate of CHR or CCGR after addition of homoharringtonine to STI571 are assessed.

EXAMPLE 1

Response to Homoharringtonine of Cells From Patients Relapsing on STI571 Therapy Peripheral blood specimens are obtained after informed consent from patient with chronic myelogenous leukemia and Ph-positive acute lymphocytic leukemia. Samples are collected before initiation of STI571 and at the time of hematologic relapse. Total leucocytes are separated by red-cell lysis and cryopreserved in liquid nitrogen until processed for testing. The response of progenitor cells from patients in blast crisis relapsing on STI571 therapy was investigated by CFU-GM assays in the presence or absence of STI571 or homoharringtonine.

CFU-GM assays: Mononuclear cells (MNC) are separated on lymphoprep (Nycomed, Oslo, Norway) from above cryopreserved peripheral blood leucocytes, and plated at 50,000 cells/mL in Iscoves' methylcellulose medium supplemented with 20 ng/mL recombinant human interleukin-3, homoharringlonine was added to the methylcellulose at the required concentration. Colonies of at least 50 cells are visualized and counted on an inverted microscope on day 14 after plating. All clonogenic assays are done in duplicate or triplicate.

Results; Interestingly, there appeared to be negligible STI571-mediated inhibition of colony formation in material obtained before treatment with the drug, with the in vitro response to STI571 not significantly different from that exhibited by cells collected at relapse. In contrast, significant sensitivity to homoharringtonine was observed in progenitors from these patients both before and after relapse, strongly implying that in CML blast crisis cells refractory to STI751 there is no significant cross-resistance to homoharringtonine.

EXAMPLE 2

Drug Combination Analyses for Demonstration that the Synergistic Effect is Stronger in STI571-resistant Cells that in Sensitive Cells For the evaluation of the combination of homoharringtonine with STI571, the median effect isobolographic method of Chou and Talabay is utilized, [Ref 19] via the computer program CalculSyn (Biosoft, Cambridge, UK). The endpoint for these analyses is derived from the cell proliferation assays (MTS) essentially as described below, but incorporating a third set of replicates where cells are exposed to constant-ratio combinations of the test drug with STI571. The combination ratios are selected, where possible, such that both drugs are in a range relevant to their achievable serum concentrations. STI571-sensitive and resistant cells are exposed to doubling dilutions of homoharringtonine over a wide range (Table 1). The degree of inhibition of cell proliferation in this assay relative to unexposed controls is designated the 'effect', which ranged from 0.0 (no inhibition (a proliferation) to 1.0 (no cellular conversion of the MTS reagent, denoting complete cell death). The effects of homoharringtonine treatments are plotted and analyzed to produce computed estimations of the relative responses to either homoharringtonine alone or in combination. In this way it is possible to detect synergistic, additive or antagonistic effects. Duplicate or triplicate independent experiments are set up for each cell line/drug combination. In each case the analysis generates plots of CI (Combination Index) versus effect. A CI value of 0.9–1.1 denotes an additive combination, whilst CI>1.1 denotes antagonistic interaction, and CI<0.9 indicates synergism between the homoharringtonine and STI571. These values are most relevant at high effect levels, as this is the desired physiological level of effect. Subsequently the CI curves can be represented as the average CI values at effects 0.5, 0.75 and 0.9 (IC50, IC75 and IC90 respectively).

TABLE 1

| DRUG | Concentrations tested | | COMBINATION DRUG:STI571 RATIO | Drug concentration in serum |
|---|---|---|---|---|
| | as single drug | in combination with 1☐M STI571 | | |
| HHT | 18.3, 183.2, | 36.6 nM 915.8 nM | 1:27.3 | 36.6 nM |
| STI571 | 1 µM | N/A | N/A | 1.46–4.6 µM |

Cell Proliferation Assay (MTS)

Cell proliferation is monitored with the CellTiter 96® AQ$_{ueous}$ One Solution Cell Proliferation Assay (Promega, UK). Cultures for the first experiments with each cell line and drug are set up with 1×10⁵ cells/mL in tissue culture flasks. Proliferation is assessed on aliquots taken daily from days 1 to 4 in order to establish the most representative time-point. Replicate experiments are thereafter set up by plating the cells directly into 96-well plates and staining with MTS on day 3. A minimum of 95% viability as assessed by Trypan blue staining is required for the initiation of any experiment. For each cell line 50 ☐l of a cell suspension in RF10 are seeded at 1×10⁵ cells/mL into flat-bottomed wells (1×10⁴ cells/well), to which is added 50 ☐l of a 2× drug dilution in RF10. Blank wells contained 100 µL RF10. All samples are plated in quadruplicate. The plate is incubated at 37° C., 5% $CO_2$ in a humid environment. On day 3, 20 µL of MTS reagent is added to each well, and the plate is re-incubated for a further 3–4 hours for stain development. At the end of this period, the plates are gently agitated and the absorbance of each well at 490 nm is recorded on an automatic microplate reader (MRX, Dynatech, Billingshurst, UK). Averaged blank values (no cells, no drug) are subtracted from sample values, and these corrected $A_{490}$ values are calculated as percentages of the control cultures grown in the absence of drug. Error bars indicate the range defined in duplicate experiments, and significant differences considered as those which fell outside the region of overlap in the ranges of the means. Such an approach is supported by the non-parametric Mann-Whitney U test.

TABLE 2

Average CI (Combination index) values at $F_A$ values of 0.5, 0.75 and 0.9, where $F_A$ denotes fraction affected (i.e. an $F_A$ of 0.2 is equivalent to a 20% reduction in cell proliferation). Threshold values are as follows: CI > 1.1 denotes antagonism, CI 0.9–1.1 denotes additivity, and CI < 0.9 denotes synergy.

| Ratio | K562-s | K562-r | LAMA84-s | LAMA84-r |
|---|---|---|---|---|
| HHT (STI571:HHT = 27.3:1) | 1.1 | 0.6 | 1.2 | 0.6 |

Conclusion: HHT is apparently additive if not mildly antagonistic in K562-s and LAMA84-s, but clearly synergistic in their STI571-resistant counterparts.

EXAMPLE 3

Case of a Patient Treated by Homoharringtonine Plus Cytarabine After a Severe Intolerance to STI571 (Glyvec)

Purpose of the study. We describe salvage therapy with homoharringtonine and low-dose daily Ara-C in a French patient (#14, Mrs. Tar. Fr. Treated by Dr. HM), with accelerated phase of chronic myelogenous leukemia (CML) intolerant to STI571 which was accrued in July 2000.

Description. A female patient, age 43, with in accelerated phase chronic myelogenous leukemia (time to progression to accelerated phase: 36 months) experienced severe hepatic intolerance after two courses of STI571. The patient was resistant to interferon alpha, BCNU, HU at the time of initiation of induction with homoharringtonine (2.5 mg/m²/day, 15 days). After white blood cell and platelet counts recovery, ten further 7-day cycles of homoharringtonine combined with cytarabine (Ara-C) 10 mg (flat dose) daily, were administered. An average of 7 days of daily Ara-C per 28-day cycle was used (see treatment plan of FIG. 1).

Results. After the second cycle of therapy, all symptoms of disease and side-effects attributable to preceding treatment disappeared. The period of aplasia was 24 days during which treatable infection occurred. Mouth ulceration and alveolar hemorrhage related to cytarabine was experienced which, despite the continuation of homoharringtonine, resolved after stopping Ara-C and institution of corticosteroids. There were no non-hematologic adverse events attributable to homoharringtonine during the one-year period of therapy. Complete hematologic response was maintained for one-year. However, cytoaenetic response was minor and transient.

Figure 2:
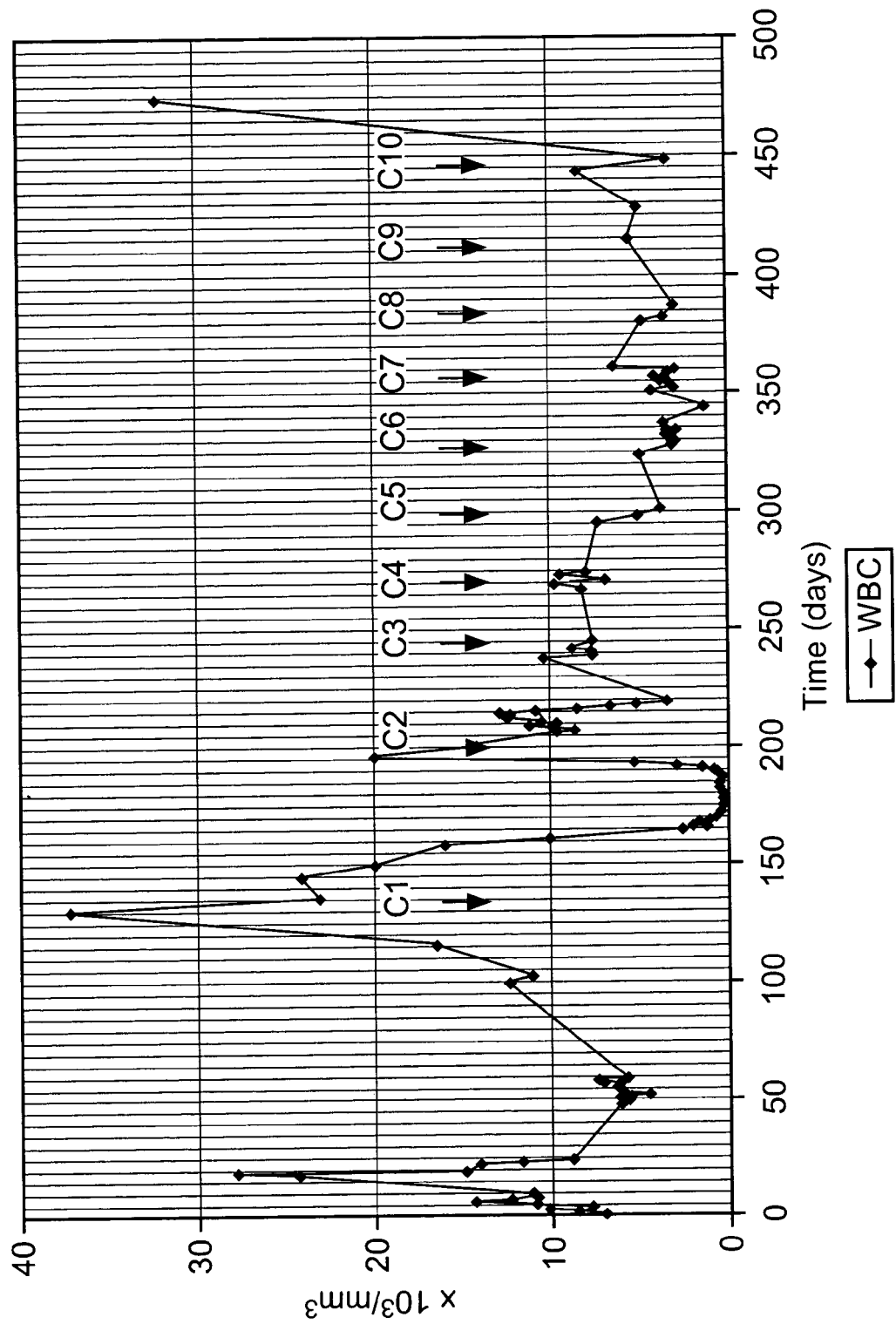
FIG. 2 is a graph of the white blood cell (WBC) count over time in the case of a patient treated by homoharringtonine plus cytarabine during a one year period after a severe intolerance to STI571: La Roche-Sur-Yon; Patient #14. Tar. Fr., F, Age 43: Accelerated phase Chronic Myelogenous Leukemia (Diagn: >15% Peripheral, Resistant To INF+Ara-C, HU, BCNU then Serious Hepatic Cytolysis Under STI571). White Blood Cell count Follow-up

Conclusion: For this patient in accelerated phase CML with a severe liver intolerance to STI571, the combination of intravenous homoharringtonine with Ara-C was uniquely efficient and well-tolerated Scheme Mrs. Tar. Fr.; C1 is first cycle of treatment with homoharringtonine The white blood cell (WBC) count over time in the case of the patient in Example 3 is shown in FIG. 2.

EXAMPLE 4

Case of a Patient Successively Resistant to Five Drugs, Including STI571

Mr. MG (patient #15), age 44 was previously treated for an advanced chronic phase of Philadelphia positive chronic myelogenous leukemia. After a debulking treatment with hydroxyurea, a combination of interferon alpha (5 MU/m$^2$/day) and low-dose cytarabine was administered according to a standard regimen (subcutaneous mode of administration, 15 mg/m$^2$/day, daily, permanently). Then, to maintain hematologic response at the initial level, cytarabine regimen was increased to intermediate dose (200 mg/m$^2$/day). White blood cells (WBC) count increasing indicated a first relapse under interferon alpha. A new investigational therapy with farnesyl transferase inhibitor (i.e. FTI from Schering Plough Laboratory) induced a transient peripheral blood response. The new oral agent STI571 was used, as fourth line therapy, at an 800 mg daily dose. A partial hematologic response was obtained with peripheral blood normalization. However a third relapse occurs quickly with STI571. Finally, a treatment based on homoharringtonine alone was initiated. At the time of initiation of homoharringtonine treatment, WBC count was 31,000/µL: 2.5 mg/m$^2$/day, 14 days. At day 17, the WBC decreased to 2,400/µL. A second wave of WBC increasing was stopped by a second cycle of homoharringtonine. Then a stabilization occurred at a level of WBC count between 3,000 and 4,500 /µL. (see scheme) for one month (at the time of evaluation). However, due to persistence of some clinical signs, the hematologic response was partial. In conclusion, homoharringtonine given as single agent is able to induce clearly a partial hematologic response in a patient resistant successively to interferon alpha, hydroxyurea, cytarabine. FTI and STI571.

Figure 3:
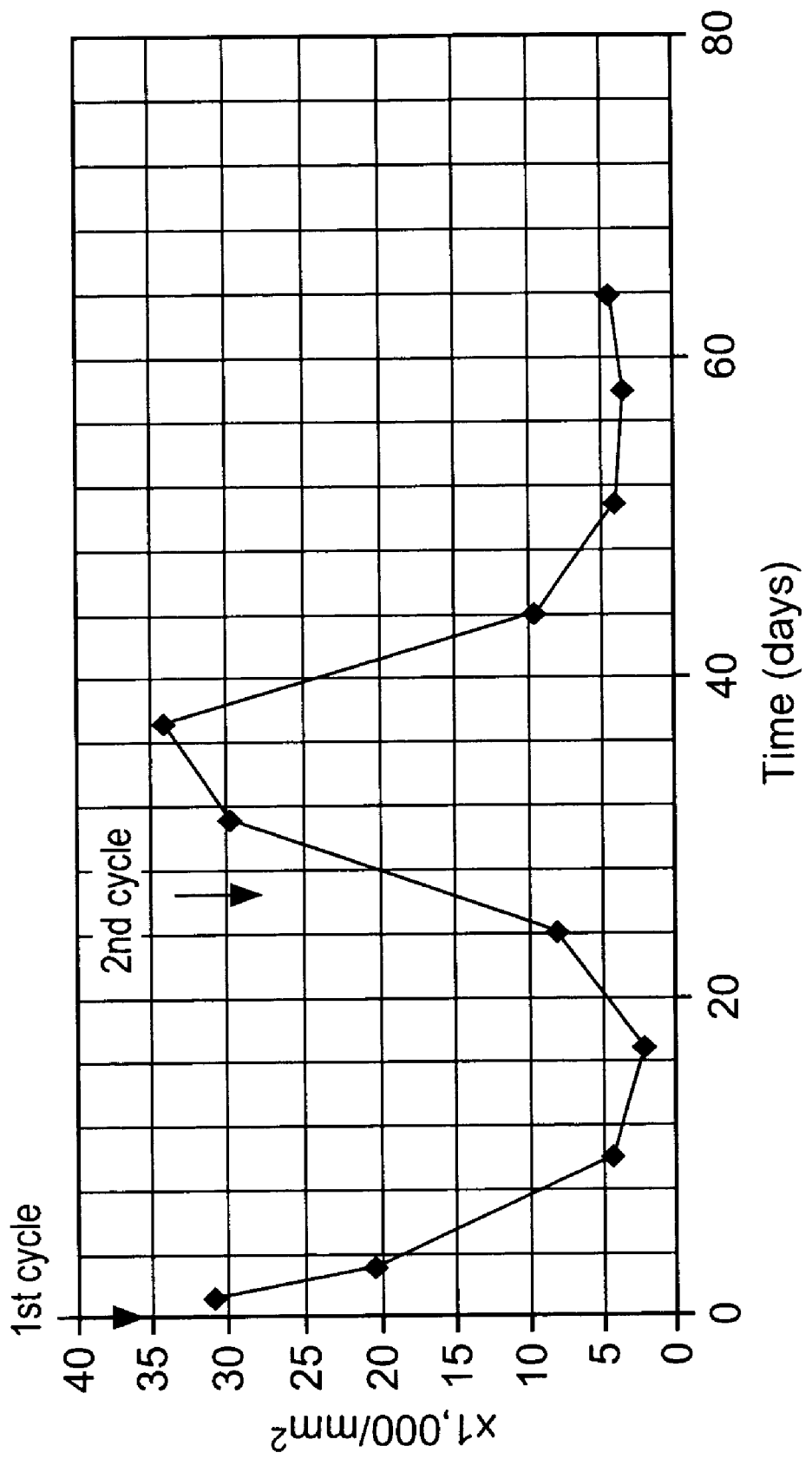
FIG. 3 is a graph of the while blood cell (WBC) count over time in the case of a patient successively resistant to five drugs including STI571, treated by homoharringtonine: Patient #15, MG, M, Age 44, treated with homoharringtonine. Chronic Phase CML (Diagn.: Resistant To INF 5 MU/Day+Ara-C 200 mg/m2/D; HU; Farnesyl transferase inhibitor (FTI); then STI571 at 600 mg then 800 mg/day: hematologic failure). WBC Count Follow-up

The white blood cell (WBC) count over time in the case of this patient of Example 4, is shown in FIG. 3.

EXAMPLE 5

Figure 4:
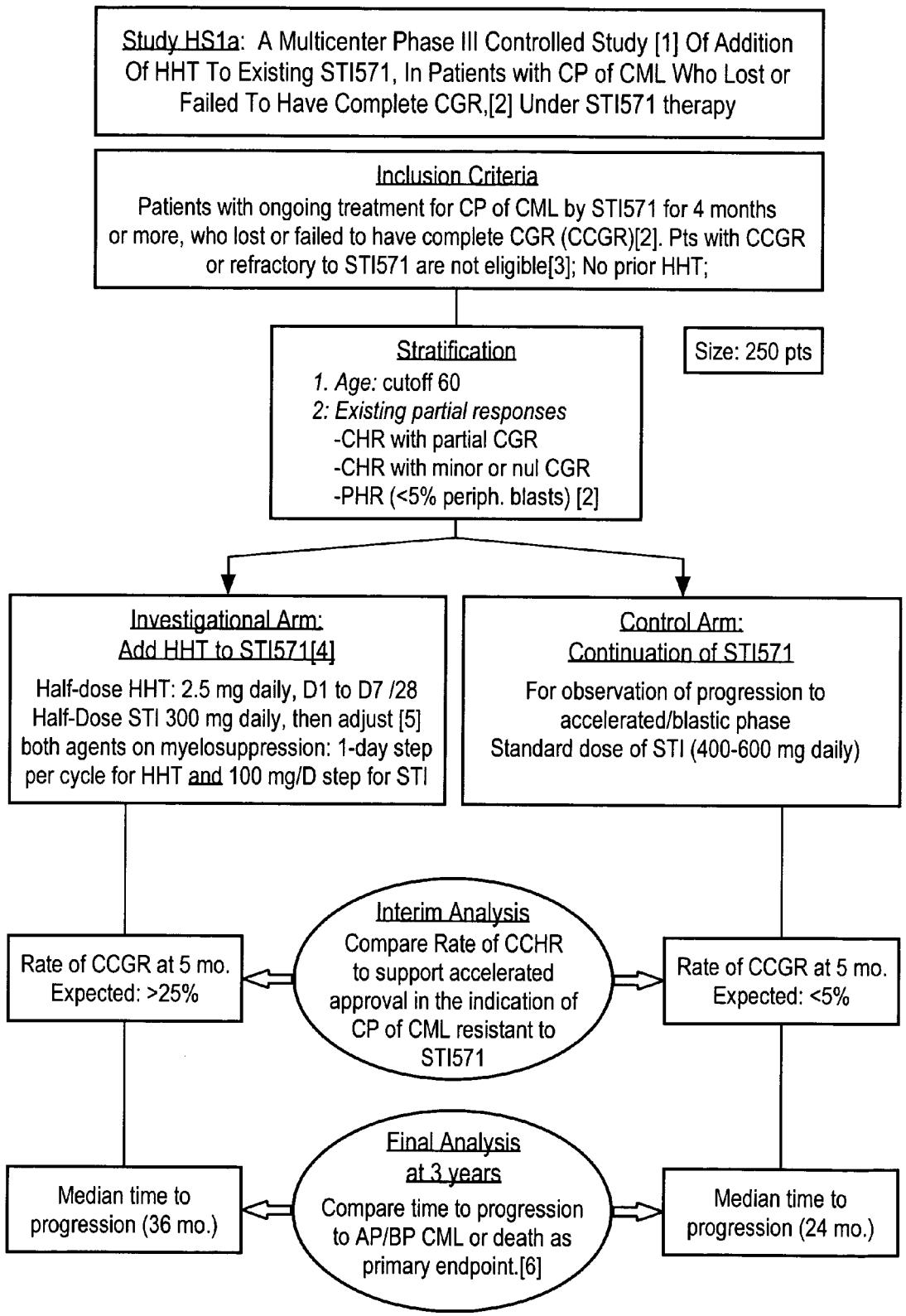
FIG. 4 is a plan of a multicenter Phase III controlled study of addition of HHT to existing STI571 therapy, in patients with CP of CML who lost or failed to have complete cytogenetic response (CGR), under STI571 therapy.

Study HS1a A controlled phase III study of {addition of homoharringtonine to STI571 vs. observation of continuation of STI571 alone} In Patients with Chronic Phase of CML who lost or failed to have a complete CCR After 4 months or more under STI571 therapy (see FIG. 4).

Rational: Patients with chronic phase of CML and under ongoing treatment for 4 months or more exclusively by STI571 alone, who lost or failed to have a complete cytogenetic response (CCGR), are randomized for addition of homoharringtonine to STI571 and compared to observation of continuation of ongoing treatment with STI, in control arm. Time to progression to accelerated or blistic phase (after 15 months on STI571, the actuarial risk of progression to AP or BP is >30%) or patient death are used as endpoint for standard approval. An interim analysis of the rate of CCGR (or recovering of) after 4 months of addition of homoharringtonine to STI571 are used to support accelerated approval in the same study. Optionally the same study could be performed in using the investigational arm only to support accelerated approval (HS1b study), if a well-controlled study able to isolate effect of homoharringtonine for survival is ongoing with an active accrual at the time of approval (i.e. in another phase of the same disease).

Size: 120×2 patients (or 120 pts in the single arm version of the study, HS1b study).

Inclusion Criteria: Philadelphia chromosome positive patients; characteristics of chronic phase; Age >18; no extramedullar disease; No prior homoharringtonine; Patients must have an ongoing treatment for CP of CML for 4 months or more by STI571 alone therapy at the time of inclusion, and patient must lost or failed to have CCGR with this ongoing STI571 treatment. Prior INF+/−Ara-C before STI571 is allowed.

Stratification: Age (cutoff 60). Time from diagnosis (cutoff 12 months); Categories of existing response during treatment with STI571 for assessment of prognosis factors: four strata: 1. CHR, 2. NEL (CHR with cytopenia), 3. No CHR/NEL, without cytopenia; 4. No CHR/NEL but cytopenia.

Treatment: Patient with an ongoing treatment by STI571 alone for chronic phase CML (i.e. 400–600 mg daily) are enrolled in the study for randomization between investigational arm for sequential additive homoharringtonine therapy (addition of homoharringtonine to existing STI) or control arm for observation of continuation of STI. In investigational arm, STI571 dose are reduced to 300 mg daily and, simultaneously, the induction with homoharringtonine are instituted by addition or homoharringtonine treatment (2.5 mg/m$^2$, D1 to D6) to so reduced STI. From the second cycle of homoharringtonine, STI571 rule of dose adjusting are used in both arms according to myelosuppression by step of +/−(100 mg of daily STI571 coupled with 2-day monthly of homoharringtonine). For example, 400 mg daily/8 days or 200 mg daily/4 days. Unless in case of grade 3–4 non hematologic adverse event attributable to one agent, dose of the two agents must be never adjusted separately. Rule of dose reducing STI571 or homoharringtonine related to each drug are used for any serious and/or uncontrollable non hematologic side effect attributable to each agent.

Assessment criteria: Time to progression to accelerated or blastic phase, since the date of addition or homoharringtonine to STI571 alone is compared to continuation of STI571 alone are assessed as primary endpoint to support standard approval. Rate of CCGR after 4 months of addition of homoharringtonine to STI571 in investigational arm are compared to continuation of STI571 alone in control arm, as secondary endpoint. In addition, CCGR of each patient of treatment arm are compared to itself before and after addition of homoharringtonine. These two kinds of response comparison of homoharringtonine+STI571 vs. STI571 are assessed by two interim analyses at 4 months (first after an accrual of 60 pts, second after an accrual of 120 patients) and used to support accelerated approval with the same study. In the single arm version of the study, only historical comparison of the rate of CCGR after addition of homoharringtonine to STI571 are assessed for the purpose of supporting of accelerated approval only.

FIG. 4 provides a plan of the multicenter Phase III controlled study of addition of HHT to existing STI571 therapy, in patients with CP of CML who lost or filed to have complete cytogenetic response (CGR), under STI571 therapy according to Example 5. FIG. 4 further includes reference numbers [1] to [6] corresponding to the following notes:

1. The same design could be used for a single-arm study in using the rational of the investigational arm only.

2. Complete cytogenetic response (CCGR) may be defined as absence of Philadelphia chromosome CHR includes: normal blood count in bone marrow and peripheral blood plus absence of clinical sign of CML, including organomegaly. PHR allows persistence of a few immature elements in peripheral blood (<5%) and splenomegaly (<50% of baseline)

3. CP-CML Patients with progression to AP/BP CML (32% at 15 months) are not included. For AP CML, see other study.

4. The continuation of STI571 therapy in patients partially resistant to this agent will prevent emergence of resistant clones: the same approach was previously used when Ara-C was combined to homoharringtonine in patients with advanced CP of CML resistant to (interferon alpha+Ara-C): median time to survival was >50 months with homoharringtonine+Ara-C versus 30 months for homoharringtonine alone.

5. Dose reduction is based on previous clinical experience of various combinations based on homoharringtonine in maintenance treatment of CML: with interferon alpha (IFN), dose of homoharringtonine was reduced to 4 days/28-day cycle and IFN to 1.67 MU daily instead 8.5 MU (divided by 5); with Ara-C, homoharringtonine dose was reduced to 5 days/28-day cycle and Ara-C at 75 mg/m2/month (Kantarjian) instead of 200–300 mg (Sokal); with Ara-C+IFN (triple combination) homoharringtonine was reduced to 2 days/month and Ara-C to 35 mg/m2/month only (in maintenance). For rule of adjusting see accelerated phase study.

6. For the purpose of standard approval.

EXAMPLE 6

Study HS2a A multicenter phase III controlled study of {sequential addition of homoharringtonine to STI} versus {observation of STI571 alone} in patients treated for AP of CML who lost or failed to have a major hematologic response.

Rational: Patients previously treated for accelerated phase CML since at least 2 month by STI571 at standard dose (600–800 mg daily), who failed to have or who lost their CHR or NEL are enrolled in the study for a two-arm randomization of observation (control arm) versus addition of homoharringtonine in investigational arm. The rate of CHR induced by each treatment (i.e. {sequential-additive STI571 plus homoharringtonine} and {STI571 alone}will compared each other (see below) and, to isolate the effect of homoharringtonine, each patient are historically compared to itself when previously treated by STI571 alone). An interim analysis of the rate of CHR (or recovering of) after 3 months of addition of homoharringtonine to STI571 are used to support accelerated approval and rate of survival at 2 years are used for standard approval.

Size: 80×2 pts.

Inclusion Criteria: Philadelphia chromosome positive patients; 10 to 29% blast in PB or BM; no extramedullar disease; Prior STI571 therapy for at least 2 months; no prior intensive chemotherapy for CML; Patients having a total failure with prior STI571 treatment (STI571 stopping for absence/loss of hematologic response) or patients with CHR or NEL under STI571 are not eligible.

Stratification: Age (cutoff 60). Categories of existing response during treatment with STI571 (RCP; PHR).

Treatment methods: Patient treated with STI571 alone for chronic phase CML (i.e. 400–600 mg daily) for at least 2 months, are enrolled in the study for randomization. In investigational arm, sequential homoharringtonine therapy is administered by addition of homoharringtonine to existing STI. Thus, STI571 dose are decreased of one step of 200 mg daily and, at the same time, the induction with homoharringtonine are instituted by addition of daily dose of homoharringtonine (starting dose: 2 mg, flat dose, daily permanently). Adjust homoharringtonine daily dose on myelosuppression until continuous (permanent) regimen with both drugs, by growing infrequency of injections of homoharringtonine (i.e. 2 mg every two-day, etc.).

Then STI571 rule of dose adjusting is used in both arms according to myelosuppression in keeping the same rate of STI/homoharringtonine, irrespective of homoharringtonine in the homoharringtonine arm. Use rule of STI571 or homoharringtonine for any serious and/or uncontrollable non hematologic side effect.

Assessment criteria: Time to progression to blastic phase and rate of survival at 30 months since the addition of homoharringtonine to STI571 alone are compared to continuation of STI571 alone, as primary endpoint to support standard approval. Rate of CHR after 3 months of addition of homoharringtonine to STI571 in investigational arm are compared to observation of continuation of STI571 alone in control arm, as secondary endpoint. In addition, the CHR of each patient of treatment arm is compared to itself before and after addition of homoharringtonine. These two kinds of response comparison of homoharringtonine+STI571 vs. STI571 are assessed by two interim analyses of response at 2 months (first after an accrual of 80 pts, second after an accrual of 160 patients) and used to support accelerated approval with the same study. In a single arm version of this study (HS2b), only historical comparison of the rate of CCGR after addition of homoharringtonine to STI571 are assessed for the purpose of supporting of accelerated approval only if a controlled study is ongoing in another setting.

EXAMPLE 7

Study HS2b A multicenter phase II single-arm study of sequential addition of homoharringtonine to existing STI571 alone therapy in patients treated for accelerated phase of CML, who lost or failed to have a major hematologic response (see FIG. 5).

Rational. Patients treated for accelerated phase CML for at least 2 months by STI, who lost or failed to have a major hematologic response (i.e. CHR and NEL), but who have a minimal hematologic response under STI, are enrolled in the study for addition of homoharringtonine to their existing STI571 therapy. Patients are stratified according to their levels of existing response under STI571 therapy. To accurately isolate the effect of homoharringtonine, every patient must have previously completed their hematologic response (stable WBC and differential counts), or must have disease progression. Patients refractory to STI571 (i.e. primary resistance to) are not eligible. The assessment of the rate of MHR (or recovering of) after 3 months of addition of homoharringtonine to STI571 is proposed to support accelerated approval.

Size: 80 pts;

Inclusion Criteria: Philadelphia chromosome positive patients; Age >18; 10 to 29% blasts in peripheral blood (PB) or bone marrow (BM); no extramedullar disease; no prior intensive chemotherapy for CML; no prior homoharringtonine; Prior STI571 therapy for at least 2 months. Patients must have disease progression or at least have completed their maximal hematologic response before to enter in the study by comparison of two WBC counts performed 2 weeks before the enrollment in the study (median time to hematologic response to STI is one month only). Patients having a primary resistance to prior STI571 treatment (STI571 stopping for absence/loss of hematologic response) or patients with CHR or NEL under STI571 are not eligible.

Stratification: Age (cutoff 60). Categories (2) of existing response during treatment by STI571 (return to chronic phase, RCP) or (peripheral blood response only, PBR).

Treatment methods: Existing STI571 dose are reduced to 400 mg daily (or 300 mg for elderly patients >60) and, at the same time, the induction with homoharringtonine are instituted by addition of daily dose of homoharringtonine: 2.5 mg/m$^2$ daily, D1 to D8 (or D1 to D6, for elderly). Number of day of homoharringtonine are adjusted on myelosuppression in keeping the same rate of STI571 daily dose/homoharringtonine monthly doses, by step of +/-(100 mg of daily STI571 coupled with 2-day monthly of homoharringtonine). For example, in case of cytopenia, standard above regimen are reduced to 300 mg daily STI571 and 6-day (D1 to D6) of homoharringtonine. Unless in case of grade 3–4 non hematologic adverse event attributable to one agent, dose of the two agents must never be adjusted separately. Rule of dose reducing of STI571 or homoharringtonine related to each drug are used for any serious and/or uncontrollable non hematologic side effect attributable to each agent.

Assessment criteria: Rate of (CHR+NEL) after 3 months of addition of homoharringtonine to STI571 is assessed for the purpose of accelerated approval (if a controlled study is ongoing with an active accrual at the time of approval request).

FIG. 5 provides a plan of the multicenter Phase II single arm study of sequential addition of HHT, in patients with an ongoing treatment by STI571 for AP of CML, who lost or failed to have a major hematologic response according to Example 7. FIG. 5 further includes reference numbers [1] to [7] corresponding to the following notes:

1. The same design could be used in theory for a controlled study: Randomization is performed for addition of homoharringtonine in investigational arm versus observation of continuation of STI571 in control arm. Analysis of the rate of MHR at 3 months is used for accelerated approval. Then final analysis of survival (or time to progression to blastic phase) supports standard approval in the same study.

2. Major Hematologic Response (MHR) may be defined as complete hematologic response (CHR) or non evidence of leukemia (NEL) CHR includes: normal blood count in bone marrow and peripheral blood plus absence of clinical sign of CML, including organomegaly. NEL includes definition of CHR but with residual cytopenia. All other responses are considered as failure.

3. Peripheral Blood Response (PBR) may be defined as peripheral blood feature of CHR only (peripheral blasts <5%)

4. The continuation of STI571 therapy in patients partially resistant to this agent will prevent emergence of resistant clones: the same approach was previously used when Ara-C was combined to homoharringtonine in patients with advanced CP of CML resistant to (interferon alpha+Ara-C): median time to survival was >50 months with homoharringtonine+Ara-C versus 30 months for homoharringtonine alone.

5. Dose reduction is based on previous clinical experience of various combinations based on homoharringtonine in maintenance treatment of CML: with interferon alpha (IFN), dose of homoharringtonine was reduced to 4 days/28-day cycle and IFN to 1.67 MU daily instead 8.5 MU (divided by 5); with Ara-C, homoharringtonine dose was reduced to 5 days/28-day cycle and Ara-C at 75 mg/m2/month (Kantarjian) instead of 200–300 mg (Sokal); with Ara-C+IFN (triple combination) homoharringtonine was reduced to 2 days/month and Ara-C to 35 mg/m2/month only (in maintenance).

6. For safety during induction, myelosuppression as endpoint for stopping STI+homoharringtonine is defined by ANC<1,000/µL and/or PLT<50,000/µL (to anticipate the myelosuppressive effect of homoharringtonine Next cycle with both drugs is resumed when ANC>1,500/µL and PLT>75,000/µL. As long as a myelosuppression endpoint is not encountered in the course of a given induction cycle, a new induction cycle of both agents (continuous STI571 and intermittent homoharringtonine), are resumed in function of the nadir of the preceding cycle. Then, treatment is continued for maintenance as follow: after recovering blood counts (ANC>1,500/µL and PLT>75,000/µL), STI571 alone is resumed at the same dose of the preceding cycle then, in case of blood count decreasing (WBC and/or PLT count), the ruler of dose decreasing for STI571 alone is applied. In case of stable and normal blood count with STI571 alone, a cure of homoharringtonine in using half-dose of the dose used in the last induction cycle is given monthly. In case of blond count increasing over the normal count (WBC or PLT count), or more than 50% of peripheral blasts or (blast+promylocyte) over the baseline, a new cycle induction with homoharringtonine is resumed and the schedule is continued as above.

7. Most MHR are expected to be obtained after only 1 cycle of homoharringtonine treatment (7days).

EXAMPLE 8

Study HS3 A multicenter phase II single-arm study of sequential addition of homoharringtonine to existing STI571 alone therapy in patients treated for blastic phase of CML, who lost or failed to have a major hematologic response.

Rational: Patients with an on-going treatment by STI571 for non-lymphoid blastic phase of CML who lost or tailed to have major hematologic response (i.e. CHR or NEL) will receive homoharringtonine in addition of their ongoing STI571 therapy. Efficacy of addition of homoharringtonine is access by comparison of the rate of (CHR+NEL) before and after addition of homoharringtonine to STI571 (expected: 30%). This study are suitable to isolate the effect of addition of homoharringtonine on response (not survival), therefore only usable to support accelerated approval if a well-controlled study capable to assess effect of homoharringtonine on survival is ongoing with an active accrual at the time of approval request.

Inclusion Criteria: Philadelphia chromosome positive patients; 30% blast or more in PB or BM; no extramedullar disease; no prior intensive chemotherapy for CML; no total failure with prior STI571 treatment (STI571 stopping for total absence/loss of hematologic response); 1 month or more of ongoing treatment by STI571 alone; patients with CHR or NEL under STI571 are not eligible.

Stratification: Age (Cutoff 60). Categories of existing response during treatment with STI, return to chronic phase (RCP); partial hematologic response (PHR).

Treatment methods: see HS2b study in AP of CML

Assessment criteria: see HS2b study in AP of CML HS2 study is started as soon as the assessment of homoharringtonine in AP CML with STI571 treatment failure is completed (compassionate use in France). As soon as a difference of rate or CHR between the two homoharringtonine arms in HS2 study (patients without CHR) is statistically significant, the less efficient arm is stopped (putatively in homoharringtonine-alone arm).

EXAMPLE 9

Compassionate Use of Homoharringtonine Combined With STI571, In Patients With Advanced Phases of Chronic Myeloid Leukemia Who Relapse Successively From Interferon-Alpha and Optionally from Cytarabine and/or Hydroxyurea, Then from STI571 Therapy Seven (7) valuable patients (pts), 3 Females and 4 males, with accelerated (6pts) or advanced chronic phase (1 pt) of Philadelphia chromosome positive chronic myeloid leukemia (CML, for underlined terms, see below definitions) all resistant to interferon alpha (IFN) combined or not with cytarabine were previously treated by imatinib mesylate (STI571, Gleevec, Glyvec) as the only one commercially available therapy for patients no longer eligible for IFN therapy or bone marrow transplantation or stem cell transplantation. After a median time of 11 months on STI571, all selected patients exhibited hematologic resistance to STI571. In despite of such resistance, and based on the result obtained in the examples 1, 2 and 7 of this invention, further therapy based upon STI571 was maintained, then, all relapsed patients were treated by addition of homoharringtonine (HTT, 2.5 mg, per square meter of body surface area per day, divided in two subcutaneous injections a day, one week). Induction included 7 days of HHT therapy per 28-day cycle (added to existing STI571), [1] whereas maintenance included 3–4 days of HHT therapy per 28-day cycle. Both drugs, were stopped in case of appearance of serious myelosuppression (leucopenia and/or thromboxytopenia and/or anemia), then both drugs were resumed after blood count recovering. Among the seven (7) valuable patients none of them experienced non-hematologic serious adverse event, four (all with accelerated phase CML) exhibited a complete hematologic remission (CHR see below definition), including one with a minor cytogenetic response and one with disappearance of additional cytogenetic anomalies. Three patients were resistant and both drugs were stopped.

[1]STI571 daily dose was reduced from 600 m to 400 mg

Definition of Terms Used in This Example

Chronic Myeloid Leukemia is defined as "a myeloproliferative disease that originates in an abnormal pluripotential bone marrow stem cell and is consistently associated with a Philadelphia (Ph) chromosome and/or the BCR/ABL fusion gene". (as recently published World Health Organization classification of tumors).

Accelerated phase of CML is defined by the presence of one or more of the following (i) a percentage of blasts in blood or bone marrow $\geq 10\%$ and $>20\%$ or (ii) a percentage of blasts plus promyelocytes in peripheral blood or bone marrow $\geq 20\%$ or (iii) a peripheral basophils rate $\geq$ or (iv) a thrombocytopenia $<100 \times 10^9/l$ unrelated to therapy or (v) a progressive splenomecaly while on Imatinib to a size $\geq 10$ cm below the left costal margin, to be confirmed on 2 occasions at least 4 weeks apart, or (vi) a 50% increase in size below the left costal margin over 4 weeks extramedullary disease outside liver or spleen. Accelerated phase of CML is a serious condition of the disease.

Chronic Phase of CML is defined as none of the criterias above defined for accelerated phase. Recent studies indicate that relapse on STI571 is a more serious condition of the disease than previous relapse on IFN.

Resistance to Imatinib to STI571 is defined as a persistence of hematologic features consistent with CML in accelerated phase in newly diagnosed patients after three months or treatment with Imatinib administered at a daily dose of 400 to 800 mg or appearance/reappearance of features consistent with accelerated phase in subjects who have previously achieved an hematologic response to STI571.

Complete Hematologic Remission (CHR) is defined as adequate bone marrow cellularity with a blast count $<5\%$ and granulocyte count $\geq 1.5 \times 10^9/l$ and white blood cell count $<10 \times 10^9/l$ and disappearance of all leukemia related sign and symptom including the absence of organomegaly and no evidence of extramedullary involvement.

TABLE

Homoharringronine Combined With STI571 In Patients With Advanced Phases of CML Who Relapse Successively From Interferon-Alpha Then STI571 Therapy

| Patient# | Authorization N°[2] | Date of 1st Application for HHT Therapy | Patient Name[3] (coded) | Patient Gender (male, female) | CML phases[4] | Hematologic Response[5] |
|---|---|---|---|---|---|---|
| 1 | 132642 | May 25, 2000 | DIS. Gi. | Ma | Accelerated | CHR |
| 2 | 150473 | Nov. 30, 2000 | SCH. Ma. | Fe | Accelerated | CHR |
| 3 | 151009 | Dec. 12, 2000 | GER. Gi. | Ma | Accelerated | RES[6] |
| 4 | 190916 | Mar. 26, 2002 | DER. Yv. | Ma | Accelerated | CHR[7] |
| 5 | 193481 | Apr. 30, 2002 | BOU. Ya. | Fe | Accelerated | RES |
| 6 | 193482 | Apr. 29, 2002 | ZUR. Em. | Ma | Accelerated | CHR[8] |
| 7 | 195028 | May 17, 2002 | WAN. Mu. | Fe | Chronic | RES |

[2]Patient dedicated number supplied by the French drug agency during emergency use of HHT (Temporarty Authorization of Use)
[3]Abbreviated first and last name
[4]See definition
[5]See definition. hematologic response is usually used as surrogate endpoint for prediction of survival
[6]Resistant (with transient and partial hematologic response) or refractory (non responding) patients
[7]Including minor cytogenetic response (partial reduction of the rate of Philadelphia chromosome positive bone marrow cells)
[8]Including disappearance of additional cytogenetic anomalies References:
The following references, some of which have been cited in the present application, are all incorporated herein by reference.
1. Kantadjian, H. M., et al., *Chronic myelogenous leukemia—progress at the M. D. Anderson Cancer Center over the past two decades and future directions: first Emil J Freireich Award Lecture.* Clin Cancer Res, 1997. 3(12 Pt 2): p. 2723–33.
2. Kantajian, H. M., et al., *Clinical course and therapy of chronic myelogenous leukemia with interferon-alpha and chemotherapy.* Hematol Oncol Clin North Am, 1998. 12(1): p. 31–80.
3. Cortes, J. E., M. Talpaz and H Kantarjian. *Chronic myelogenous leukemia: a review.* Am J Med. 1996. 100 (5): p. 555–70.
4. Faderl, S., H. M. Kantarjian. and M. Talpaz, *Chronic myelogenous leukemia: update on biology and treatment.* Oncology (Huntingt), 1999. 13(2): p. 169–80; discussion 181, 184.
5. Silver, R. T., et al., *An evidence-based analysis of the effect of busulfan, hydroxyurea, interferon, and allogeneic bone marrow transplantation in treating the chronic phase of chronic myeloid leukemia: developed for the American Society of Hematology* [see comments]. Blood, 1999. 94(5): p. 1517–36.
6. Grem, J. L., et al., *Cephaloluxine esters: antileukemic advance or therapeutic failure?* J Natl Cancer Inst, 1998. 80(14): p. 1095–103.
7. Slichenmyer, W. J. and D. D. Von Hoff, *New natural products in cancer chemotherapy.* J Clin Pharmacol, 1990. 30(9): p. 770–88.
8. Novartis, Gleevec (*imatinib mesylate*), *prescribing Information: clinical studies.* Sponsor's Biochure T2001-14 90012401.2001: p. 1.
9. Goldman, J., *Personal communication.* 2001.
10. Tipping, A. J., et al., *Response of STI571-resistant cells to other chemotherapeutic drugs and signal transduction inhibitory.* Blood, 2000. Suppl. 1 abstract 420.
11. Scappini, B., et al., *In vitro effects of STI571-containing drug combinations on growth of Ph-positive myelogenous leukemia-derived cells.* Blood. 2000. Suppl. 1 abstr. 425.
12. Kano, Y., et al., *In vitro cytotoxic effects of a tyrosine kinase inhibitor STI571 in combination with commonly used antileukemic agents.* Blood, 2001. 97(7) p. 1999–2007.
13. Scappini, B., et al., *In vitro effects of STI571-containing drug combinations on growth of Philadelphia-Positive Myelogenous Leukemia Cells.* Cancer, 2001. In Press.
14. Tiping, A., et al., *Drug responses of STI571-resistant cells: synergism of STI571 with other chemotherapeutic drugs.* JNCI, submitted to, 2001.
15. Cai. Z., et al., *Apoptotic response to homoharringtonine in human wt p53 leukemic cells is independent of reactive oxygen species generation and implicates Bax translocation, mitochrondrial cytochrome c release and caspase activation.* Leukemia, 2001. 15(4): p. 567–74.
16. Sattler, M., et al., *The BCR/ABL tyrosine kinase induces production of reactive oxygen species in hematopoietic cells.* J Biol Chem, 2000. 275(32): p. 24273–8.
17. Iacobini, M., et al., *Involvement of oxygen radicals in cytarabine-induced apoptosis in human polymorphonuclear cells.* Biochem Pharmacol, 2001. 61(8): p. 1033–40.
18. Hellstrand, K., et al., *Histamine and cytokine therapy.* Acta Oncol, 1998. 37(4): p. 347–53.
19. Chou, T. C. and P. Talalay, *Quantitative analysis of dose-effect relationships: the combined effects of multiple drugs or enzyme inhibitors.* Adv Enzyme Regul, 1984. 22: p. 27–55.

What is claimed is:

1. A method of treating chronic myelogenous leukemia, a related myeloproliferative disorder or a Ph-positive acute lymphocytic leukemia in a subject animal, comprising:
   (a) selecting or identifying an animal suffering from chronic myelogenous leukemia or a related myeloproliferative disorder and showing resistance or intolerance to treatment with STI571; and
   (b) administering to the animal homoharringtonine.

2. The method of claim 1, wherein homoharringtonine is combined with one or more other antileukemic agents.

3. The method of claim 1, wherein homoharringtonine is combined simultaneously with one or more other antileukemic agents.

4. The method of claim 1, wherein homoharringtonine is combined sequentially with one or more other antileukemic agents.

5. The method of treatment of claim 1, wherein homoharringtonine is combined sequentially by addition to existing STI571 therapy, comprising the following steps (a) to (d), and optionally (e):
   (a) administering to patients with chronic myelogenous leukemia, optionally further resistant to standard interferon alpha therapy, STI571 until a complete cytogenetic response or at least a complete hematologic response is obtained;
   (b) in patients partially STI571-resistant, reducing to 300 to 400 mg daily but not removing STI571 treatment, in those patients who failed to have or lost their complete cytogenetic or hematologic response;
   (c) administering homoharringtonine subcutaneously and/or intravenously or/and orally, at a dose of 0.25 to 5 mg/m$^2$;
   (d) adjusting the homoharringtonine dose and/or STI571 dose according to cytopenia and/or side effects; and
   (e) optionally, subcutaneously or intravenously administering an oral nucleoside synergistic with homoharringtonine, wherein said oral nucleoside may be added simultaneously or sequentially to homoharringtonine.

6. The method of claim 5, wherein said oral nucleoside in step (e) is cytarabine, wherein cytarabine may be added simultaneously or sequentially to homoharringtonine.

7. A method for inhibiting proliferation of a hyperproliferative myeloid cell resistant to STI5171, comprising:
   a) contacting the cell with STI571; and
   b) contacting the cell with homoharringtonine,
wherein STI571 and homoharringtonine are provided in an amount effective to inhibit proliferation of said myeloid cell.

8. A method of treating chronic myelogenous leukemia, a related myeloproliferative disorder or a Ph-positive acute lymphocytic leukemia in a subject animal, comprising:
   a) administering to the animal in a first course of treatment STI571, wherein said CML or disorder displays resistance and/or intolerance to STI571; and
   b) administering to the animal in a second course of treatment a combination of homoharringtonine and STI571 in an amount effective to inhibit proliferation of myeloid cells.

9. The method of treatment of claim 2, wherein the other antileukemic agents are interferon alpha and/or one or more nucleosides and/or a farnesyl transferase inhibitor (FTI).

10. The method of treatment of claim 4, wherein the other antileukemic agent is interferon alpha or PEG-interferon.

11. The method of treatment of claim 4, wherein the other antileukemic agent is one or more nucleosides.

12. The method of treatment of claim 9, wherein the other antileukemic agents is a farnesyl transferase inhibitor (FTI).

13. The method of treatment of claim 11, wherein the nucleosides are cytarabine (Ara-C) and/or decitabine and/or troxacytabine.

14. The method of treatment of claim 13, wherein a nucleoside is cytarabine (Ara-C).

15. The method of treatment of claim 9, wherein the other agents are a combination of interferon alpha and cytarabine.

16. The method of treatment of claim 1, wherein the animal is a human being.

17. The method of claim 2, wherein homoharringtonine is combined with STI571.

18. The method of claim 3, wherein homoharringtonine is combined simultaneously with STI571.

19. The method of claim 3, wherein homoharringtonine is combined simultaneously with STI571 which is continued from previous treatment.

20. The method of claim 4, wherein homoharringtonine is combined sequentially with STI571.

21. The method of treatment of claim 20, wherein administration of the ST1571 is continued.

22. The method of treatment of claim 5, wherein the STI571 is administered in a dosage of 400 to 800 mg daily.

23. The method of treatment of claim 5, wherein the homoharringtonine is administered at a dose of 2.5 $mg^2$.

24. The method of treatment of claim 5, wherein the homoharringtonine is administered for 2 to 14 days per 28-day cycle.

25. The method of treatment of claim 8, wherein the animal is a human being.

* * * * *

UNITED STATES PATENT AND TRADEMARK OFFICE
CERTIFICATE OF CORRECTION

PATENT NO.       : 6,987,103 B2
APPLICATION NO.  : 10/397267
DATED            : January 17, 2006
INVENTOR(S)      : Jean-Pierre Robin et al.

It is certified that error appears in the above-identified patent and that said Letters Patent is hereby corrected as shown below:

In column 1, line 37, the term "bematologic" should be --hematologic--

In column 1, lines 43 and 45, the term "TNF" shoul be --INF--

In column 4, line 19, the term "step(c)" should be --step(e)--

In column 16, line 42, the term "tailed" should be --failed--

Col. 20, line 49, claim 7, "STI5171" should be --STI571--

Col 22, line 12 claim 23, "2.5mg$^2$" should be --2.5 mg/m$^2$--

Signed and Sealed this

Twenty-ninth Day of August, 2006

JON W. DUDAS
*Director of the United States Patent and Trademark Office*